(12) United States Patent
Man et al.

(10) Patent No.: US 12,077,726 B2
(45) Date of Patent: *Sep. 3, 2024

(54) CLEANING COMPOSITIONS EMPLOYING EXTENDED CHAIN ANIONIC SURFACTANTS

(71) Applicant: ECOLAB USA INC., Saint Paul, MN (US)

(72) Inventors: Victor Fuk-Pong Man, Saint Paul, MN (US); Derrick Richard Anderson, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/163,926

(22) Filed: Feb. 3, 2023

(65) Prior Publication Data

US 2023/0183605 A1 Jun. 15, 2023

Related U.S. Application Data

(63) Continuation of application No. PCT/US2018/014381, filed on Jan. 19, 2018, which is a continuation of application No. 15/411,213, filed on Jan. 20, 2017, now Pat. No. 11,591,546.

(51) Int. Cl.
| | |
|---|---|
| *C11D 1/29* | (2006.01) |
| *C11D 1/37* | (2006.01) |
| *C11D 1/65* | (2006.01) |
| *C11D 1/66* | (2006.01) |
| *C11D 1/94* | (2006.01) |
| *C11D 17/00* | (2006.01) |
| *C11D 1/10* | (2006.01) |
| *C11D 1/40* | (2006.01) |
| *C11D 1/44* | (2006.01) |
| *C11D 1/90* | (2006.01) |

(52) U.S. Cl.
CPC ............ *C11D 1/29* (2013.01); *C11D 1/37* (2013.01); *C11D 1/65* (2013.01); *C11D 1/66* (2013.01); *C11D 1/94* (2013.01); *C11D 17/0017* (2013.01); *C11D 1/10* (2013.01); *C11D 1/40* (2013.01); *C11D 1/44* (2013.01); *C11D 1/90* (2013.01)

(58) Field of Classification Search
None
See application file for complete search history.

(56) References Cited

U.S. PATENT DOCUMENTS

| | | | | |
|---|---|---|---|---|
| 6,191,099 B1* | 2/2001 | Crutcher | ............ | C11D 1/65 510/499 |
| 7,387,900 B2* | 6/2008 | Tamarkin | ........... | A61K 47/6923 436/525 |
| 7,387,990 B2 | 6/2008 | Dettmann et al. | | |
| 2006/0211593 A1 | 9/2006 | Hand et al. | | |
| 2011/0073802 A1* | 3/2011 | Haag | ................ | A01N 33/08 252/175 |
| 2012/0066839 A1 | 3/2012 | Man et al. | | |
| 2012/0066840 A1 | 3/2012 | Man et al. | | |
| 2014/0041131 A1 | 2/2014 | Man et al. | | |
| 2014/0274854 A1 | 9/2014 | Ortmann et al. | | |

FOREIGN PATENT DOCUMENTS

| | | |
|---|---|---|
| EP | 0087914 A1 | 9/1983 |
| EP | 0332805 A2 | 9/1989 |
| EP | 0332805 A3 | 9/1989 |
| EP | 0368146 A2 | 5/1990 |
| EP | 0573341 B1 | 7/1998 |
| FR | 2329746 | 5/1977 |
| JP | 63073140 A | 4/1988 |
| JP | 1100442 A | 4/1989 |
| JP | 10292199 A | 11/1998 |
| JP | 2001246339 A | 9/2001 |
| JP | 2009210514 A | 9/2009 |
| WO | 9612000 A1 | 4/1996 |
| WO | 199732962 A1 | 9/1997 |
| WO | 9928423 A1 | 6/1999 |
| WO | 199927054 A1 | 6/1999 |
| WO | 200068348 A1 | 11/2000 |
| WO | 2004044110 A1 | 5/2004 |
| WO | 2006041704 A1 | 4/2006 |
| WO | 2007064525 A1 | 6/2007 |

(Continued)

OTHER PUBLICATIONS

European Patent Office in connection with European patent No. 18742383.5 filed Jul. 15, 2019, "Extended European Search Report", 11 pages, mailed Oct. 5, 2020.
Venable et al., "A Microemulsion Cosurfactant with excellent water solubilization at high oil content" Journal of Dispersion Science and Technology, vol. 5, No. 1, pp. 73-80, 1984.
Ecolab USA Inc., PCT/US2018/014381 filed Jan. 19, 2018, "The International Search Report and Written Opinion of the International Searching Authority, or the Declaration", 10 pages, May 30, 2018.
Product Information: Lonzabac, 2 pages, 2002.
Singh, H.N. et al., "Water Solubilization in Microemulsions Containing Amines as Cosurfactant", JAOCS, vol. 70, No. 1, pp. 69-73. Jan. 1993.

(Continued)

*Primary Examiner* — Tanisha Diggs
(74) *Attorney, Agent, or Firm* — McKee, Voorhees & Sease, PLC

(57) ABSTRACT

The invention discloses synergistic combinations of surfactant blends and cleaning compositions employing the same. In certain embodiments a surfactant system is disclosed which includes an extended anionic surfactant with novel co-surfactants including one or more of an alkyl glycerol ether, an ethoxylated alkyl glycerol ether, an alcohol ethoxylate and/or a gemini surfactant. This system forms emulsions with, and can remove greasy and oily stains, even those comprised of non-trans fats. The compositions may be used alone, as a pre-spotter or other pre-treatment or as a part of a soft surface or hard surface cleaning composition.

10 Claims, 4 Drawing Sheets

(56) References Cited

FOREIGN PATENT DOCUMENTS

| WO | 2007101470 A1 | 9/2007 |
|---|---|---|
| WO | 2010086821 A2 | 8/2010 |
| WO | 2013062127 A1 | 5/2013 |

OTHER PUBLICATIONS

Barber, J.A.S., et al., "Fluorescent Tracer Technique for Measuring the Quantity of Pesticide Deposited to Soil Following Spray Applications", Crop Protection, vol. 22, pp. 15-21, 2003.

Bergervoet, P.W.M., et al., "Application of the Forensic Luminol for Blood in Infection Control", Journal of Hospital Infection, vol. 68, pp. 329-333, 2008.

Carling, Philip C., et al., "Improved Cleaning of Patient Rooms Using a New Targeting Method", Brief Report, CID, vol. 42, pp. 385-388, 2006.

Charoensaeng, Ampira, et al., "Solubilization and Adsolubilization of Polar and Nonpolar Organic Solutes by Linker Molecules and Extended Surfactants", J. Surfact. Deterg., vol. 12, pp. 209-217, 2009.

Do, Linh D., et al., "Environmentally Friendly Vegetable Oil Microemulsions Using Extended Surfactants and Linkers", J. Surfact. Deterg., vol. 12, pp. 91-99, 2009.

Griffith, C.J., et al., "An Evaluation of Hospital Cleaning Regimes and Standards", Journal of Hospital Infection, vol. 45, pp. 19-28, 2000.

Hartel, Peter G., et al., "Exposing Water Samples to Ultraviolet Light Improves Fluorometry for Detecting Human Fecal Contamination", Water Research, vol. 41, pp. 3629-3642, 2007.

Lipscomb, I.P., et al., "Rapid Method for the Sensitive Detection of Protein Contamination on Surgical Instruments", Journal of Hospital Infection, vol. 62, pp. 141-148, 2006.

Lu, Y. F., et al., "Laser Surface Cleaning and Real-Time Monitoring", Laser Microprocessing Laboratory, National University of Singapore, pp. 331-337, 2000.

Mori, F., et al., "Equilibrium and Dynamic Behavior of a System Containing a Mixture of Anionic and Nonionic Surfactacts", Progr. Colloid. Polym. Sci., vol. 82, pp. 114-121, 1990.

Phan, Tri T., et al., "Microemulsion-Based Vegetable Oil Detergency Using an Extended Surfactant", J. Surfact. Deterg., vol. 13, pp. 313-319, 2010.

Pyrek, Kelly M., "Hospitals Can Learn from CSI Sleuthing Methods", www.infectioncontroltoday.com, 2008.

Salo, Satu, et al., "Cleaning Validation of Fermentation Tanks", Food and Bioproducts Processing, vol. 86, pp. 204-210, 2008.

Wisniewski, Karen, "Specialty Liquid Household Surface Cleaners", Research and Development, Global Technology, Colgate-Palmolive Company, pp. 463-512, 2011.

Witthayapanyanon, Anuradee, et al., "Interfacial Properties of Extended-Surfactant-Based Microemulsions and Related Macroemulsions", J. Surfact. Deterg., vol. 13, pp. 127-134, 2010.

Zhang, Hui, et al., "Lauryl Alcohol and Amine Oxide as Foam Stabilizers in the Presence of Hardness and Oily Soil", Journal of Surfactants and Detergents, vol. 8, No. 1, pp. 99-107, Jan. 2005.

"Cleaner Alcohol hand Rub Training Gel Fluorescent Gel 500ml bottle with Integral Pump Dispenser", www.my.supplychain.nhs.uk/catalogue/product/mrb180/cleanser-alcohol-hand-run-training-gel-500ml-bottle-with-integral-pump-dispenser, 1 pages, 2011.

Ecolab USA Inc., International Application No. PCT/US2010/049319 filed Sep. 17, 2010, "International Search Report", 3 pages, mailed Jun. 1, 2011.

Ecolab USA Inc., International Application No. PCT/US2010/049326, filed Sep. 17, 2010, "International Search Report", 4 pages, mailed Jun. 1, 2011.

Ecolab USA Inc., International Application No. PCT/US2010/049334, filed Sep. 17, 2010, "The International Search Report and The Written Opinion of the International Searching Authority, or the Declaration", 8 pages, mailed Jun. 21, 2011.

Ecolab USA Inc., International Application No. PCT/US2010/049338, filed Sep. 17, 2010, "International Search Report", 3 pages, mailed Jun. 28, 2011.

\* cited by examiner

CLEANING COMPOSITIONS EMPLOYING EXTENDED CHAIN ANIONIC SURFACTANTS

CROSS-REFERENCE TO RELATED APPLICATIONS

This application is a Continuation of PCT/US18/14381, filed Jan. 19, 2018, which claims priority to U.S. Ser. No. 15/411,213, filed on Jan. 20, 2017.

FIELD OF THE INVENTION

The invention relates to surfactant systems and cleaning compositions which employ synergistic combinations of components including extended chain anionic surfactants. The cleaning compositions are useful for removing a number of challenging stains including non-trans fats and fatty acids by forming emulsions and micoremulsions with such oily and greasy soils for their removal.

BACKGROUND OF THE INVENTION

Surfactants reduce the surface tension of water by adsorbing at the liquid-gas interface. They also reduce the interfacial tension between oil and water by adsorbing at the liquid-liquid interface. Surfactants are a primary component of most detergents. When dissolved in water, surfactants give a product the ability to remove soil from surfaces. Each surfactant molecule has a hydrophilic head that is attracted to water molecules and a hydrophobic tail that repels water and simultaneously attaches itself to oil and grease in soil. These opposing forces loosen the soil and suspend it in the water.

Surfactants do the basic work of detergents and cleaning compositions by breaking up stains and keeping the soil in the water solution to prevent re-deposition of the soil onto the surface from which it has just been removed. Surfactants disperse soil that normally does not dissolve in water.

Nonylphenol ethoxylates (NPEs) are predominantly used as industrial and domestic detergents as a surfactant. However, while effective, NPEs are disfavored due to environmental concerns. For example, NPEs are formed through the combination of ethylene oxide with nonylphenol (NP). Both NP and NPEs exhibit estrogen-like properties and may contaminate water, vegetation and marine life. NPE is also not readily biodegradable and remains in the environment or food chain for indefinite time periods.

An alternative to NPEs are alcohol ethoxylates (AEs). These alternatives are less toxic and degrade more quickly in the environment. However, it has recently been found that textiles washed with NPE free and phosphorous free detergents containing AEs smoke when exposed to high heat, e.g., in a steam tunnel in industrial laundry processes, or when ironed.

Surfactants are often incorporated in a cleaning composition to clean soiled surfaces. One of the preferred mechanisms is by microemulsifying these soils. Surfactants are also often incorporated into an oil-in-water microemulsion to make oil containing products appear more homogenous. These oil containing products include a variety of different surfactant systems in 5-20% solubilized oil which may be used as is, or are then diluted with water prior to use. Examples of these oil containing products include cosmetics, products containing oil for skin protections, and cleaning products containing oily solvents for degreasing such as terpene and other water immiscible solvents. The surfactant systems generally employed in these cleaning products include a mixture of anionic or non-ionic surfactants and a short chain alcohol to help solubilize the oil phase and prevent liquid crystal formation. While short chain alcohols are effective, they also contribute to the volatile organic solvent content (VOC) of the product and pose flammability problems.

As can be seen there is a continuing need to develop effective, environmentally friendly, and safe surfactants and surfactant systems that can be used in cleaners of all kinds. This is particularly so in light of several new cleaning challenges that have emerged.

Health authorities have recently recommended that trans fats be reduced or eliminated in diets because they present health risks. In response, the food industry has largely replaced the use of trans fats with non-trans fats. These types of non-trans fats are the most difficult to remove from surfaces because; 1) the high molecular weight of triglyceride oil results in more difficulty in forming either dispersions or bicontinuous structures, 2) the polyunsaturation of triglyceride oil makes it difficult to be handled by conventional surfactants, and 3) polymerization of the triglyceride oil makes it even more difficult to remove. The food industry and textile cleaning industry have also experienced an unexplained higher frequency of laundry fires. Textile items such as rags that are not effectively washed to better remove non-trans fats, Non-transfats, are prone to cause fire due their substantial heat of polymerization of the trans fats. Non-transfats have conjugated double bonds that can polymerize and the substantial heat of polymerization involved can cause fire, for example, in a pile of rags used to mop up these non-transfat soils.

As can be seen, there is a need in the industry for improvement of cleaning compositions, such as hard surface cleaners and laundry detergents and particularly the surfactants used therein so that difficult soils can be removed in a safe environmentally friendly and effective manner.

SUMMARY OF THE INVENTION

In an effort to reduce energy consumption and total water use, many large water use cleaning systems such as laundry systems in health and home care and textile care, and car wash systems need water reclaim systems. Previous foam fractionation work obtained very good results with vehicle care produced water.

Textile care produced water, however contains high levels of strongly emulsified oil. High levels of soil and detergent lead to a more challenging application.

Applicants herein provide a faster demulsification trigger, without sacrificing cleaning performance for textile cleaning and water reclamation.

The invention meets the needs above by providing a surfactant system, mixture or blend that can be used alone or as a part of a detergent, hard surface cleaner or a pre-spotting treatment. The surfactant system is capable of emulsifying and microemulsifying and thus removing, oily and greasy stains. In a preferred embodiment the surfactant compositions of the invention can remove non-transfat and fatty acid stains. Generally, non-transfats are more difficult to remove than transfats both from a cleaning and removal standpoint as well as laundry fire safety concern due to heat of polymerization of the non-trans fats. The invention is highly effective for removal of non-transfats, transfats and other oily soils, such as hydrocarbon oil.

The invention has many uses and applications which include but are not limited to: laundry cleaning, reduction of laundry fire due to non-transfats, and hard surface cleaning such as manual pot-n-pan cleaning, machine warewashing, all purpose cleaning, floor cleaning, CIP cleaning, open facility cleaning, foam cleaning, vehicle cleaning, etc. The invention is also relevant to non-cleaning related uses and applications such as dry lubes, tire dressings, polishes, etc. as well as triglyceride based lotions, suntan lotions, potentially pharmaceutical emulsions and microemulsions.

The surfactant system comprises a synergistic combination of components with an extended chain anionic surfactant. The extended anionic surfactant is preferably one with at least 5 moles of propoxylation. Most preferred is from about 5 to about 8 moles of propoxylation.

Further in a preferred embodiment the extended chain anionic surfactant is combined with a linker or co-surfactant. The co-surfactant can be a single hydrophobic tail with hydrophilic head of small effectively hydrated radius which previously included amine oxides, fatty acids, mono glycerides, long chain alcohols or the so-surfactant can have twin hydrophobic tails with hydrophilic head of "regular or large" effectively hydrated radius di-octyl sulfosuccinate, diglyceride). In a preferred embodiment the cosurfactant is one or more of the following: a linear or branched alkyl amine, alkyl diamine, and/or alkyl triamines, and alkyl oxypropyl amine, diamine, and/or triamine, and/or ethoxylated/propoxylated variants of the above, and mixtures thereof. According to the invention, applicants have identified several novel linker co-surfactants which in, combination with specific anionic extended chain surfactants provide microemulsions that are non-gelling with low viscosity and are stable indefinitely and over a wide temperature range. The novel co-surfactants include one or more of the following: a linear or branched alkyl amine, alkyl diamine, and/or alkyl triamines, alkyl oxypropyl amine, diamine, and/or triamine, including ethoxylated/propoxylated variants of the above and/or medium carbon chain length nonionic ethoxylated/propoxylated alkyl amines having low moles of alkoxylation and mixtures thereof.

In another embodiment the co-surfactant can be an extended nonionic surfactant. Extended nonionic surfactants include those of the general formula:

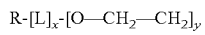

Where R is the lipophilic moiety, a linear or branched, saturated or unsaturated, substituted or unsubstituted, aliphatic or aromatic hydrocarbon radical having from about 8 to 20 carbon atoms, L is a linking group, or extended hydrophobe such as a block of poly-propylene oxide, a block of poly-ethylene oxide, a block of poly-butylene oxide or a mixture thereof; x is the chain length of the linking group ranging from 1-25; and y is the average degree of ethoxylation ranging from 1-20. Applicant has found that when L is PO the superior extension length is between 5 and 8 moles of PO. In a more preferred embodiment the extended nonionic surfactants include Guerbet alcohol alkoxylates, such as $C_{10}$ Guerbet $(PO)_8EO_x$ where x is 3, 6, 8, or 10) or linear $C_{12-14}(PO)_{16}(EO)_x$ (x=6, 12, 17). These extended nonionic surfactants reduce or eliminate the need for a cosurfactant when used to form emulsions and microemulsions. Further yet, Applicant has found that capping the extended surfactants, such as with about 1-5 moles of $(R-[L]_x-EO_yPO_{(1-5)})$ or with an alkyl group such as methyl, butyl, benzyl etc. can create stable emulsions with lower foam profiles. Other surfactants that are useful include Gemini surfactants.

In certain embodiments the surfactants system is part of a cleaning composition which further includes a multiply charged cation such as $Mg^{2+}$, $Ca^{2+}$ or other functional electrolyte such as an alkalinity source or a chelating agent. The resultant combination is highly effective at forming emulsions and microemulsions with non-transfats at relatively low temperatures. This system can be used in formulations for laundry detergents, hard surface cleaners, whether alkali or acid based, or even by itself as a pre-spotting agent.

In a further aspect of the present invention, a laundry detergent composition is provided which includes the surfactant system of the invention, a builder and an enzyme; the laundry detergent product being adapted to readily dissolve and disperse non trans fats in commercial, industrial and personal laundry washing processes or in a pre-spotting treatment. These and other objects, features and attendant advantages of the present invention will become apparent to those skilled in the art from a reading of the following detailed description of the preferred embodiment and the appended claims.

Figure 1:
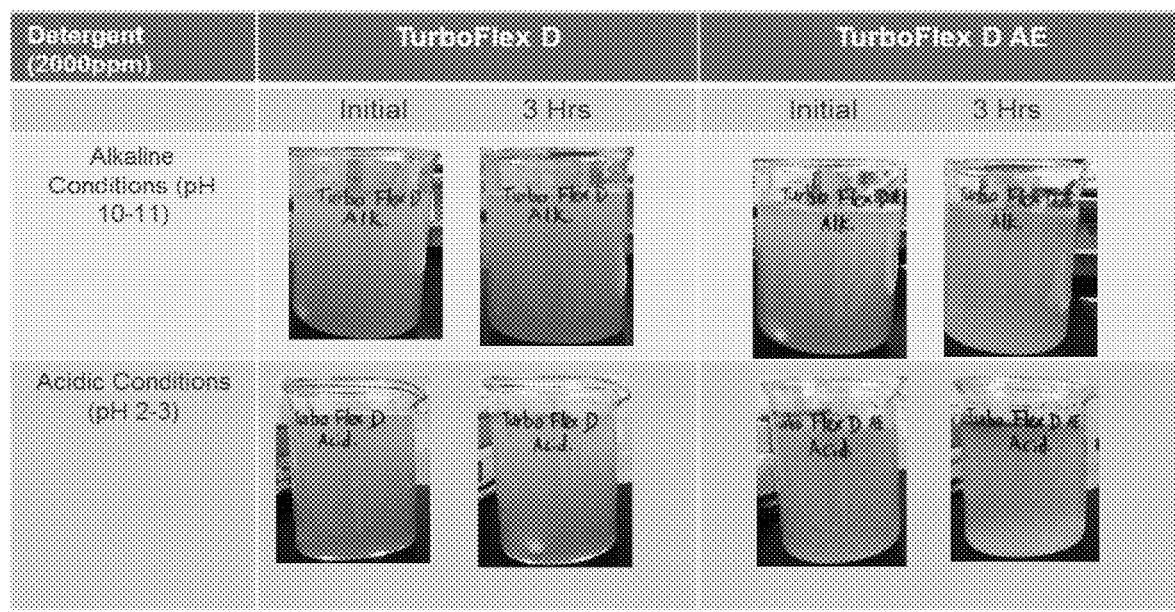
FIG. 1 is a photograph of water after 2000 ppm detergent was added to oil present in cleaning water. The water contains high levels of strongly emulsified oil. Residual water with high levels of soil and detergent lead to a more challenging application. One can see that after 3 hours, in both acid and alkaline conditions, the oils remain suspended.

These data explain the emulsion/microemulsion at alkaline pH (where X-AES and the amine cosurfactant work synergistically to microemulsify the soybean oil), and the pair demulsify at neutral and acidic pH (where the pair work antagonistically due to the protonated amine/anionic neutralization).

DETAILED DESCRIPTION OF THE INVENTION

So that the invention maybe more readily understood, certain terms are first defined and certain test methods are described.

As used herein, "weight percent," "wt-%", "percent by weight", "% by weight", and variations thereof refer to the concentration of a substance as the weight of that substance divided by the total weight of the composition and multiplied by 100. It is understood that, as used here, "percent", "%", and the like are intended to be synonymous with "weight percent", "wt-%", etc.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "surfactant" as used herein is a compound that contains a lipophilic segment and a hydrophilic segment, which when added to water or solvents, reduces the surface tension of the system.

An "extended chain surfactant" is a surfactant having an intermediate polarity linking chain, such as a block of poly-propylene oxide, or a block of poly-ethylene oxide, or a block of poly-butylene or a mixture thereof, inserted between the surfactant's conventional lipophilic segment and hydrophilic segment.

The term "electrolyte" refers to a substance that will provide ionic conductivity when dissolved in water or when in contact with it; such compounds may either be solid or liquid.

As used herein, the term "microemulsion" refers to thermodynamically stable, isotropic dispersions consisting of nanometer size domains of water and/or oil stabilized by an interfacial film of surface active agent characterized by ultra-low interfacial tension.

It should be noted that, as used in this specification and the appended claims, the singular forms "a", "an", and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

The term "hard surface" refers to a solid, substantially non-flexible surface such as a counter top, tile, floor, wall, panel, window, plumbing fixture, kitchen and bathroom furniture, appliance, engine, circuit board, and dish.

The term "soft surface" refers to a softer, highly flexible material such as fabric, carpet, hair, and skin.

As used herein, the term "cleaning" refers to a method used to facilitate or aid in soil removal, bleaching, microbial population reduction, and any combination thereof.

"Soil" or "stain" refers to a non-polar oily substance which may or may not contain particulate matter such as mineral clays, sand, natural mineral matter, carbon black, graphite, kaolin, environmental dust, etc.

As used herein, the term "cleaning composition" includes, unless otherwise indicated, detergent compositions, laundry cleaning compositions, hard surface cleaning compositions, and personal care cleaning compositions for use in the health and beauty area. Cleaning compositions include granular, powder, liquid, gel, paste, bar form and/or flake type cleaning agents, laundry detergent cleaning agents, laundry soak or spray treatments, fabric treatment compositions, dish washing detergents and soaps, shampoos, body washes and soaps, and other similar cleaning compositions. As used herein, the term "fabric treatment composition" includes, unless otherwise indicated, fabric softening compositions, fabric enhancing compositions, fabric freshening compositions and combinations thereof. Such compositions may be, but need not be rinse added compositions.

The term "laundry" refers to items or articles that are cleaned in a laundry washing machine. In general, laundry refers to any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated.

Exemplary treated fibers include those treated for flame retardancy. It should be understood that the term "linen" is often used to describe certain types of laundry items including bed sheets, pillow cases, towels, table linen, table cloth, bar mops and uniforms. The invention additionally provides a composition and method for treating non-laundry articles and surfaces including hard surfaces such as dishes, glasses, and other ware.

Surfactant Systems Employing Extended Chain Anionic Surfactants

The surfactant system or mixture of the invention employs one or more extended chain anionic surfactants. Extended surfactants have an intermediate polarity polyalkylene oxide chain (or linker) such as polyoxypropylene, and polyoxybutylene inserted between the lipophilic tail group and hydrophilic polar head, which may be anionic or nonionic.

Examples of lipophilic tail groups include hydrocarbons, alkyl ether, fluorocarbons or siloxanes. Examples of anionic hydrophilic polar heads of the extended surfactant include, but are not necessarily limited to, groups such as sulfate, polyoxyethylene sulfate, ethoxysulfate, carboxylate, ethoxycarboxylate, phosphate, ethoxyphosphates. Examples of nonionic hydrophilic polar heads of the extended surfactant include, but are not necessarily limited to, groups such as polyoxyethylene, C6 sugar, xylitol, di-xylitol, ethoxy-xylitol, and glucose.

Anionic extended surfactants generally have the formula:

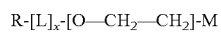

Where L is a linking group, such as a block of poly-propylene oxide, a block of poly-butylene oxide or a mixture thereof; x is the chain length of the linking group ranging from 2-25; and y is the average degree of ethoxylation ranging from 0-10; M is any ionic species such as carboxylates, sulfonates, sulfates, and phosphates. A cationic species will generally also be present for charge neutrality such as hydrogen, an alkali metal, alkaline earth metal, ammonium and ammonium ions which may be substituted with one or more organic groups.

These extended chain surfactants attain low interfacial tension and/or high solubilization in a single phase microemulsion with oils, such as nontrans fats with additional beneficial properties including, but not necessarily limited to, insensitivity to temperature and irreversibility. For example, in one embodiment the emulsions may function over a relatively wide temperature range of from about 20 to about 280° C., alternatively from about 20 to about 180° C. (350° F.).

Many extended chain anionic and nonionic surfactants are commercially available from a number of sources. Table 1 is a representative, nonlimiting listing of several examples of the same.

TABLE 1

| Extended Surfactants | Source | % Active | Structure |
|---|---|---|---|
| Plurafac SL-42(nonionic) | BASF | 100 | $C_{6-10}$-$(PO)_3(EO)_6$ |
| Plurafac SL-62(nonionic) | BASF | 100 | $C_{6-10}$-$(PO)_3(EO)_8$ |
| Lutensol XL-40(nonionic) | BASF | 100 | (3 propyl heptanol Guerbet alcohol series) |
| Lutensol XL-50(nonionic) | BASF | 100 | $C_{10}$-$(PO)_a(EO)_b$ series, where a is 1.0 to 1.5, and b is 4 to 14. |
| Lutensol XL-60(nonionic) | BASF | 100 | |
| Lutensol XL-70(nonionic) | BASF | 100 | |
| Lutensol XL-79(nonionic) | BASF | 85 | |
| Lutensol XL-80(nonionic) | BASF | 100 | |
| Lutensol XL-89(nonionic) | BASF | 80 | |
| Lutensol XL-90 (nonionic) | BASF | 100 | |
| Lutensol XL-99 (nonionic) | BASF | 80 | |
| Lutensol XL-100 (nonionic) | BASF | 100 | |
| Lutensol XL-140 (nonionic) | BASF | 100 | |
| New Lutensol XL surfactant designed by Ecolab | BASF | 100 | C10 Guerbet alcohol $(PO)_8(EO)_3$ |
| New Lutensol XL surfactant designed by Ecolab | BASF | 100 | C10 Guerbet alcohol $(PO)_8(EO)_6$ |
| New Lutensol XL surfactant designed by Ecolab | BASF | 100 | C10 Guerbet alcohol $(PO)_8(EO)_8$ |
| New Lutensol XL surfactant designed by Ecolab | BASF | 100 | C10 Guerbet alcohol $(PO)_8(EO)_{10}$ |
| Ecosurf EH-3 (nonionic) | Dow | 100 | 2-Ethyl Hexyl $(PO)_m(EO)_n$ series |
| Ecosurf EH-6 (nonionic) | Dow | 100 | |
| Ecosurf EH-9(nonionic) | Dow | 100 | |
| Ecosurf SA-4(nonionic) | Dow | 100 | $C_{6-12}$ $(PO)_{3-4}$ $(EO)_4$ |
| Ecosurf SA-7 (nonionic) | Dow | 100 | $C_{6-12}$ $(PO)_{3-4}$ $(EO)_7$ |
| Ecosurf SA-9 (nonionic) | Dow | 100 | $C_{6-12}$ $(PO)_{3-4}$ $(EO)_9$ |
| Surfonic PEA-25(nonionic) | Huntsman | 100 | $C_{12-14}(PO)_2N[(EO)_{2.5}]_2$ |
| X-AES (anionic) | Huntsman | 23 | $C_{12-14}$-$(PO)_{16}$-$(EO)_2$-sulfate |
| X-LAE6 (nonionic) | Huntsman | 100 | $C_{12-14}$-$(PO)_{16}(EO)_6$ |
| X-LAE12 (nonionic) | Huntsman | 100 | $C_{12-14}$-$(PO)_{16}(EO)_{12}$ |
| X-LAE17 (nonionic) | Huntsman | 100 | $C_{12-14}$-$(PO)_{16}(EO)_{17}$ |

TABLE 1-continued

| Extended Surfactants | Source | % Active | Structure |
|---|---|---|---|
| Alfoterra 123-4S (anionic) | Sasol | 30 | $C_{12-13}$-$(PO)_4$-sulfate |
| Alfoterra 123-8S (anionic) | Sasol | 30 | $C_{12-13}$-$(PO)_8$-sulfate |
| Marlowet 4561 (nonionic under acidic condition, anionic under alkaline condition) | Sasol | 90 | $C_{16-18}(PO)_4(EO)_5$-carboxylic acid |
| Marlowet 4560 (nonionic under acidic condition, anionic under alkaline condition) | Sasol | 90 | $C_{16-18}(PO)_4(EO)_2$-carboxylic acid |
| Marlowet 4539 (nonionic under acidic condition, anionic under alkaline condition) | Sasol | 90 | Iso C9-$(PO)_2EO_2$-carboxylic acid |
| LP-6818-41-IP2 | Exp | 100 | $C_{12-14}$-$(PO)_4$ |
| LP-6818-41-IP3 | Exp | 100 | $C_{12-14}$-$(PO)_6$ |
| LP-6818-41-IP4 | Exp | 100 | $C_{12-14}$-$(PO)_8$ |
| LP-6818-47-IP5 | Exp | 100 | $C_{12-14}$-$(PO)_4(EO)_{12}$ |
| LP-6818-47-IP6 | Exp | 100 | $C_{12-14}$-$(PO)_4(EO)_{14}$ |
| LP-6818-47-IP7 | Exp | 100 | $C_{12-14}$-$(PO)_4(EO)_{16}$ |
| LP-6818-49-FB | Exp | 100 | $C_{12-14}$-$(PO)_4(EO)_{18}$ |
| LP-6818-51-IP1 | Exp | 100 | $C_{12-14}$-$(PO)_6(EO)_{14}$ |
| LP-6818-51-IP2 | Exp | 100 | $C_{12-14}$-$(PO)_6(EO)_{16}$ |
| LP-6818-53-IP3 | Exp | 100 | $C_{12-14}$-$(PO)_6(EO)_{18}$ |
| LP-6818-53-FB | Exp | 100 | $C_{12-14}$-$(PO)_6(EO)_{20}$ |
| | Exp | | |
| LP-6818-66-IP2 | Exp | 100 | TDA-$(PO)_4$ |
| LP-6818-67-IP3 | Exp | 100 | TDA-$(PO)_4(EO)_8$ |
| LP-6818-67-IP4 | Exp | 100 | TDA-$(PO)_4(EO)_{10}$ |
| LP-6818-67-IP5 | Exp | 100 | TDA-$(PO)_4(EO)_{12}$ |
| LP-6818-68-IP5 | Exp | | |
| LP-6818-68-IP6 | Exp | 100 | TDA-$(PO)_4(EO)_{14}$ |
| LP-6818-68-FB | Exp | 100 | TDA-$(PO)_4(EO)_{18}$ |
| | Exp | 100 | $C_{12-14}$-$(PO)_{20}(EO)_2$ |
| | Exp | 100 | $C_{12-14}$-$(PO)_{20}(EO)_4$ |
| | Exp | 100 | $C_{12}$-$(PO)_{20}(EO)_6$ |
| Isofol 12 PO5EO5 | Exp | 100 | Guerbet $C_{12}$-$(PO)_5(EO)_5$ |
| Isofol 12 PO5EO8 | Exp | 100 | Guerbet $C_{12}$-$(PO)_5(EO)_8$ |
| Isofol 12 PO8EO5 | Exp | 100 | Guerbet $C_{12}$-$(PO)_8(EO)_5$ |
| Isofol 12 PO8EO8 | Exp | 100 | Guerbet $C_{12}$-$(PO)_8(EO)_8$ |
| Capped Triton DF-12 | DOW | 100 | $C_{8-10}$-$(PO)_2(EO)_{11}$-Benzyl |
| Plurafac SLF-180 | BASF | 100 | C10 Guerbet alcohol $(PO)_3(EO)_{10}(PO)_{10}$ |

In a preferred embodiment the extended chain surfactant is an anionic extended chain surfactant with at least 5 moles of propoxylation.

Co-Surfactant

According to the invention, an anionic extended chain surfactant is employed in synergistic combination with a linear or branched alkyl amine, alkyl diamine, and/or alkyl triamines, and alkyl oxypropyl amine, diamine, and/or triamine, and/or extended medium carbon chain length nonionic ethoxylated/propoxylated variants of the above having low moles of ethoxylation and mixtures thereof as a cosurfactant.

The co surfactant component can include those which may be represented by the following general formula

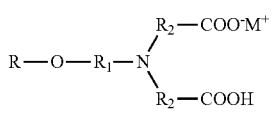

in which, R represents a $C_4$ to $C_{24}$ alkyl group, and is preferably a $C_{10}$ to $C_{16}$ alkyl group, $R_1$ and $R_2$ independently represent a $C_1$ to $C_8$ alkyl group, is preferably —CH$_2$CH$_2$— or —CH$_2$CH$_2$CH$_2$—, and M may be any salt-forming anion which permits water solubility or water miscibility of the compound, e.g., chloride, bromide, methosulfate, ethosulfate, lactate, saccharinate, acetate or phosphate. Such compounds are presently commercially available, such as those marketed in the Tomamine Amphoteric series of amphoteric surfactants, ex. Air Products Inc.

Additional amphoteric surfactants that can be used include, but are not limited to, imidiazolines and imidiazoline derivatives, betaine derivatives, amphoacetate derivatives, propionates, and mixtures thereof.

Exemplary betaine surfactants include those which may be represented by the general formula:

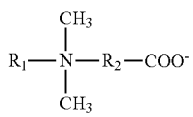

wherein $R_1$ is an alkyl group containing from 8 to 18 carbon atoms, or the amido radical which may be represented by the following general formula:

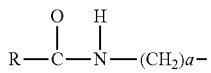

wherein R is an alkyl group having from 8 to 18 carbon atoms, a is an integer having a value of from 1 to 4 inclusive, and $R_2$ is a C1-C4 alkylene group. Examples of such water-soluble betaine surfactants include dodecyl dimethyl betaine, as well as cocoamidopropylbetaine.

One or more amphoacetates such as sodium lauroamphoacetate, or diamphoacetates may also be used. Amphoacetates may be represented by the following general formula:

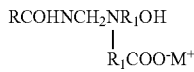

and, diamphoacetates may be represented by the following general formula:

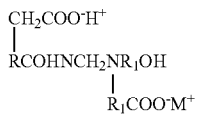

wherein in both formulas, R represents an aliphatic group having 8 to 18 carbon atoms, $R_1$ represents an aliphatic group having 1 to 5 carbon atoms, but is preferably —CH$_2$—, or —CH$_2$CH$_2$—, and M is a cation such as sodium, potassium, ammonium, or a substituted ammonium. Examples of such compounds include: sodium lauroamphoacetate, sodium cocoamphoacetate, disodium lauroamphoacetate, and disodium cocoamphoacetate. In a preferred embodiment the composition is substantially free of sodium cocoamphoacetate and cocoamidoproyl hydroxysultaine which may reduce the antimicrobial activity of the cationic active compound.

In additional embodiments the cosurfactant includes an amine or Examples of amines or amine derivatives may include the reaction product of alkylpropylene diamine with glutamic acid called GLUCOPROTAMIN, N-cocotrimethylenediamine, dodecylmorpholine-N-oxide, alkylpropylenediamine, and N-Alkyl(C12-14)dimethylamine oxide, commercially available as Lonzabac®12 (e.g., Lonzabac 12.100).

Accordingly, in one example, the amine may be a primary, secondary, or tertiary amine. An example tertiary alkyl amine that can be used is an amine with the general formula:

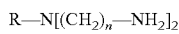

where R is a $C_4$-$C_{20}$ alkyl, such as a $C_6$-$C_{18}$ alkyl, a $C_5$-$C_{10}$ alkyl, a $C_6$-$C_{10}$ cycloalkyl, a $C_7$-$C_{10}$ aryl alkyl, such as a $C_7$ aryl alkyl, a $C_6$-$C_{14}$ aryl group, and where n is a number ranging from 2 to 10, such as 2 to 6, or 2 or 3. In some examples, R is a $C_6$-$C_{18}$, alkyl group, such as a dodecyl or tallow fat alkyl group.

The co-surfactant is an additive which "sticks to" or "associates with" the extended chain anionic surfactant and links it with the molecules in the bulk phase, and hence increase the "reach" of the surfactant molecules which are adsorbed at interface, thus enhancing their performance. The choice among the different co-surfactants includes considerations involving foam, pH, the type of surface to be cleaned, the cleaning temperature and the like. For example, under acid or alkaline conditions, the dioctyl sulfosuccinate can rapidly degrade while amine oxide does not. The co-surfactant can be a single hydrophobic tail with hydrophilic head of small effectively hydrated radius such as amine oxides, fatty acids, mono glyceride, potentially long chain alcohol or a twin hydrophobic tails with hydrophilic head of "regular or large" effectively hydrated radius di-octyl sulfosuccinate, diglyceride).

In further embodiments the amine co-surfactant may be employed with additional co-surfactants including amine oxide or dioctyl sulfosuccinate or a co-surfactant such as alkyl glycerol ether, monoglycerides, diglycerides, fatty acids or fatty diacids, short chain alcohols with low moles of ethoxylation and/or gemini surfactants.

Glycerol Ethers

The glycerol ethers used in the context of the present invention are mono- or dialkylated derivatives of glycerol. These compounds are generally known in the state of the art.

Thus, according to a first aspect, the subject matter of the invention is the use of a glycerol ether of formula:

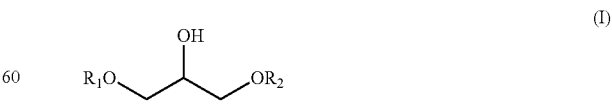

in which:
$R_1$ represents an alkyl group having from 1 to 18 carbon atoms; $R_2$ represents a hydrogen atom or an alkyl group having from 1 to 18 carbon atoms, preferably a methyl or ethyl group; as a cosurfactant.

A first preferred family of glycerol ethers capable of being used in the context of the present invention is composed of the compounds of abovementioned formula (I) in which:

$R_1$ represents an alkyl group of general formula $C_xH_2x+1$ where x=1 to 9;

$R_2$ represents an alkyl group of general formula $C_yH_2y+1$ where y=0 to 8; and observing the condition $4 \leq x+y \leq 10$.

One family of glycerol ethers capable of being used in the context of the present invention is composed of the monoalkylated glycerol compounds of abovementioned formula (I), in which: $R_3$ represents an alkyl group having from 4 to 9 carbon atoms; and $R_2$ represents a hydrogen atom.

A preferred family of glycerol ethers capable of being used in the context of the present invention is composed of the dialkylated glycerol compounds of abovementioned formula (I), in which: $R_1$ represents a methyl or ethyl group; and $R_2$ represents a methyl or ethyl group.

A particularly preferred family of glycol ethers includes of one or more glycerol monoalkyl ether(s) of the general formula

R—O—CH$_2$—CHOH—CH$_2$OH in which R is a branched or unbranched $C_3$-$C_{18}$-alkyl group, where the alkyl group can be substituted by one or more hydroxyl and/or $C_1$-$C_4$-alkoxy group(s) and/or the alkyl chain can be interrupted by up to four oxygen atoms.

Particularly preferred is the 3-alkoxy-1,2-propanediols. The glycerol monoalkyl ethers according to the invention can be present as racemate (D,L) or in the form of enantiomer-enriched mixtures of the D- or L-form, or in the form of the pure enantiomers.

In one particularly preferred embodiment, the alkyl chain is interrupted by up to 4 oxygen atoms, is therefore introduced by an alcohol group which is accessible from an alcohol or diol by reaction with ethylene oxide and/or propylene oxide. In another embodiment, the alkyl group is a hydrocarbon group.

Here, the alkyl chain in the alkyl group R of the glycerol monoalkyl ether can contain alkyleneoxy groups, such as, for example, ethyleneoxy and/or propyleneoxy groups.

The alkyl group preferably contains 6 to 12 carbon atoms, particularly preferably 6 to 10 carbon atoms, in particular 8 carbon atoms, e.g. a preferred alkyl group is a hydrocarbon group having 8 carbon atoms, in particular a 2-ethylhexyl group. Thus, the particularly preferred glycerol monoalkyl ether is 3-[(2-ethylhexyl)oxy]-1,2-propanediol, which is marketed under the trade name Sensiva® SC 50 by Schulke & Mayr.

Yet another group in includes ethylene oxide/propylene oxide copolymers (Pluronics® BASF), gemini-type surfactants (Rhodia) and diphenyl ether gemini-type surfactants (DOWFAX®., Dow Chemical) discussed hereinafter.

According to the invention, the ethylene oxy or propylene oxy groups are from 0 to 3 moles of ethoxylation. The alkyl is preferably branched to increase the effective cross-sectional area of the hydrophobe.

Alcohol Ethoxylate

Additional co-surfactants include short chain ethoxylated alcohols of the formula $R_1$—(—O—CH$_2$)$_m$—OH where $R_1$ is a $C_2$-$C_{18}$ hydrocarbyl chain, and the average degree of ethoxylation m is generally from 1 to 10, preferably from 1 to 6. The alkyl chain length is preferably in the $C_6$ to $C_{14}$ range.

The alcohol may be derived from natural or synthetic feedstock.

Gemini Surfactant

In one or more embodiments, the linker co-surfactant surfactant includes a gemini surfactant. In contrast to simple surfactants, which usually consist of a single hydrophilic head and one or two hydrophobic tails, gemini surfactants have two or more head groups and two or more tails.

In general, a gemini surfactant includes at least two hydrophobic chains, at least two ionic or polar groups, and a spacer. The gemini structure may be symmetrical (i.e. the tails are identical and the heads are identical) or unsymmetrical. In one or more embodiments, the gemini surfactant includes three or four tails.

Examples of polar groups include polyethers and sugars. Examples of ionic groups include positive and negative ions. Specific examples of ionic groups include ammonium, phosphate, sulphate, and carboxylate. In one or more embodiments, the head includes one or more sulphate groups.

Examples of spacers include polar and nonpolar groups. Specific examples of spacer groups include amides, short or long methylene groups, stilbene, polyether, aliphatic, and aromatic groups. In one or more embodiments, the spacer includes a hydrocarbon chain methylene group.

In one or more embodiments, gemini surfactants may be represented by the general schematics

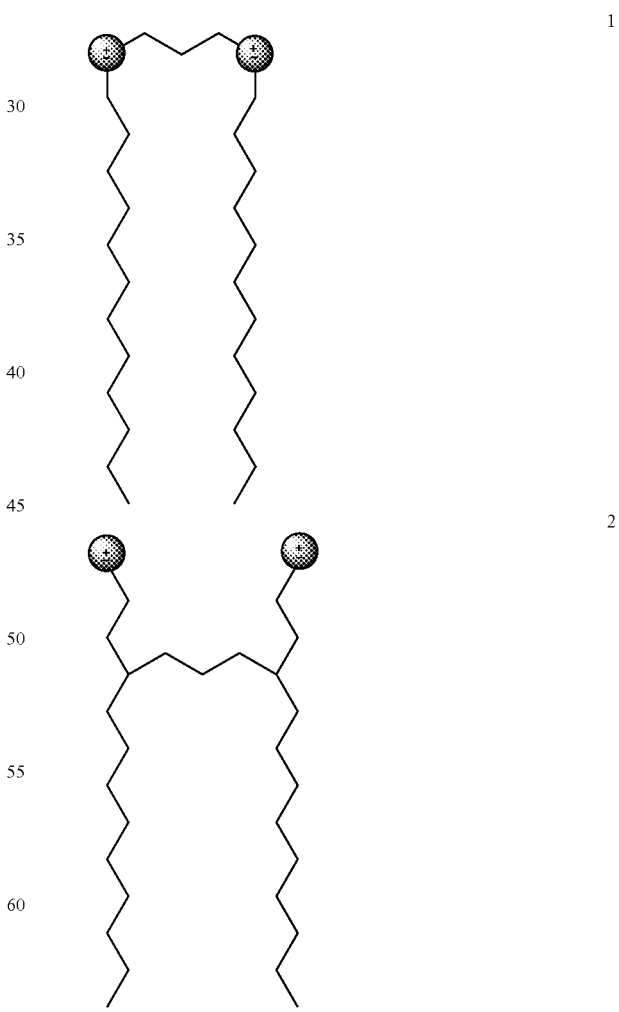

Gemini surfactants may be selected for use in the present invention based upon one or more characteristics, such as tail length, degree of branching, ionic nature of the head group, counterion type, number of heads (i.e. dimer, trimer, tetramer, and the like), spacer solubility (i.e. hydrophobic or hydrophilic), spacer length, and the molecular rigidity of the spacer. In a preferred embodiment the gemini surfactant is a foam inhibiting surfactant such as alkane diols, alkanedicarboxylic acids and esters thereof, such as the commercially-available line of ENVIROGEM® surfactants, available from Air Products and Chemicals, Inc. in Allentown, Pa. Specific examples include EnviroGem® 360, and EnviroGem® AD01.

Gemini surfactants are further described in U.S. Pat. No. 6,710,022, which is incorporated herein by reference.

According to the invention the extended anionic surfactant to the total cosurfactant is 1:5 to 5:1 percent by weight.

Cation

The surfactant system as part of a cleaning composition can further comprise a multiply charged cation such as $Mg^{2+}$, $Ca^{2+}$ and/or functional electrolytes such as an alkalinity source or one of more chelating agents when present in a cleaning composition.

The surfactant system of the invention is particularly suited for removal of most greasy and oily soils including the most difficult types of soils, non-transfats when used in a cleaning composition. This removal is accomplished without the need for alcohol components which can lead to high VOC content.

Cleaning Compositions Comprising Extended Chain Surfactants

In another embodiment the invention includes a ware wash or laundry detergent which includes a builder, and other traditional components such as enzymes. Examples of such standard laundry, warewash and rinse aid components and formulations, which are well known to those skilled in the art, are provided in the following paragraphs.

The detergent or warewash composition can be provided in solid or liquid form and includes, for example, an alkalinity source, a metal protector (for warewash), a surfactant or surfactant system of the invention water, and a threshold agent, and other optional components. Typical formulations can include form about 30% and about 80% by weight alkalinity source, between about 15% and about 35% by weight metal protector, between about 2% and about 10% by weight surfactant, between about 0.1% and about 20% by weight water, between about 0.2% and about 15% by weight threshold agent. If a scale inhibitor is present it is present in an amount of from about 0 to about 15% by weight.

In yet another embodiment, the invention employs hard surface cleaning composition with the surfactant system of the invention, an acid source or source of alkalinity, and optionally a solvent, a water conditioning agent, and water to make a hard surface cleaner which will be effective at removing greasy and oily soils from surfaces such as showers, sinks, toilets, bathtubs, countertops, windows, mirrors, transportation vehicles, floors, and the like.

These surfaces can be those typified as "hard surfaces" (such as walls, floors, bed-pans).

A typical hard surface formulation at about 18% activity includes between about 40 wt. % and about 80 wt. % surfactant system of the invention, between about 3 wt. % and about 18 wt. % water conditioning agent, between about 0.1 wt. % and about 0.55 wt. % acid or alkalinity source, between about 0 wt. % and about 10 wt. % solvent and between about 10 wt. % and about 60 wt. % water.

Particularly, the cleaning compositions include between about 45 wt. % and about 75 wt. % surfactant system of the invention, between about 0 wt. % and about 10 wt. % optional co-surfactant, between about 5 wt. % and about 15 wt. % water conditioning agent, between about 0.3 wt. % and about 0.5 wt. % acid source, between about 0 and about 6 wt. % solvent and between about 15 wt. % and about 50 wt. % water. In other embodiments, similar intermediate concentrations and use concentrations may also be present in the cleaning compositions of the invention.

In a laundry detergent formulation the compositions of the invention typically include the surfactant system of the invention, and a builder, optionally with an enzyme. Examples of such standard laundry detergent ingredients, which are well known to those skilled in the art, are provided in the following paragraphs.

Additional Components

While not essential for the purposes of the present invention, the non-limiting list of additional components illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable additional materials include, but are not limited to, surfactants, builders, chelating agents, dye transfer inhibiting agents, viscosity modifiers, dispersants, additional enzymes, and enzyme stabilizers, catalytic materials, bleaches, bleach activators, hydrogen peroxide, sources of hydrogen peroxide, preformed peracids, polymeric dispersing agents, threshold inhibitors for hard water precipitation pigments, clay soil removal/anti-redeposition agents, brighteners, suds suppressors, dyes, fabric hueing agents, perfumes, structure elasticizing agents, fabric softeners, carriers, hydrotropes, processing aids, solvents, pigments antimicrobials, pH buffers, processing aids, active fluorescent whitening ingredient, additional surfactants and mixtures thereof. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' compositions. Thus, certain embodiments of Applicants' compositions do not contain additional materials. However, when one or more additional materials are present, such one or more additional components may be present as detailed below:

The liquid detergent herein has a neat pH of from about 7 to about 13, or about 7 to about 9, or from about 7.2 to about 8.5, or from about 7.4 to about 8.2. The detergent may contain a buffer and/or a pH-adjusting agent, including inorganic and/or organic alkalinity sources and acidifying agents such as water-soluble alkali metal, and/or alkali earth metal salts of hydroxides, oxides, carbonates, bicarbonates, borates, silicates, phosphates, and/or metasilicates; or sodium hydroxide, potassium hydroxide, pyrophosphate, orthophosphate, polyphosphate, and/or phosphonate. The organic alkalinity source herein includes a primary, secondary, and/or tertiary amine. The inorganic acidifying agent herein includes HF, HCl, HBr, HI, boric acid, sulfuric acid, phosphoric acid, and/or sulphonic acid; or boric acid. The organic acidifying agent herein includes substituted and substituted, branched, linear and/or cyclic $C_{1-30}$ carboxylic acid.

Bleaching Agents—The cleaning compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxzone®, and mixtures thereof. Suitable percarboxylic acids include hydrophobic and hydrophilic peracids having the formula R—(C—O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(2) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (3) bleach activators having R—(C—O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Additional Surfactant—In some embodiments, the compositions of the invention include an additional surfactant. Additional surfactants can be anionic, nonionic, cationic zwitterionic and can also include additional extended chain surfactant as discussed herein.

The cleaning composition can contain an additional anionic surfactant component that includes a detersive amount of an anionic surfactant or a mixture of anionic surfactants. Anionic surfactants are desirable in cleaning compositions because of their wetting and detersive properties. The anionic surfactants that can be used according to the invention include any anionic surfactant available in the cleaning industry. Suitable groups of anionic surfactants include sulfonates and sulfates. Suitable surfactants that can be provided in the anionic surfactant component include alkyl aryl sulfonates, secondary alkane sulfonates, alkyl methyl ester sulfonates, alpha olefin sulfonates, alkyl ether sulfates, alkyl sulfates, and alcohol sulfates.

Suitable alkyl aryl sulfonates that can be used in the cleaning composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate.

Suitable alkane sulfonates that can be used in the cleaning composition can have an alkane group having 6 to 24 carbon atoms. Suitable alkane sulfonates that can be used include secondary alkane sulfonates. A suitable secondary alkane sulfonate includes sodium $C_{14}$-$C_{17}$ secondary alkyl sulfonate commercially available as Hostapur SAS from Clariant.

Suitable alkyl methyl ester sulfonates that can be used in the cleaning composition include those having an alkyl group containing 6 to 24 carbon atoms. Suitable alpha olefin sulfonates that can be used in the cleaning composition include those having alpha olefin groups containing 6 to 24 carbon atoms.

Suitable alkyl ether sulfates that can be used in the cleaning composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether sulfate and is available under the name Steol CS-460.

Suitable alkyl sulfates that can be used in the cleaning composition include those having an alkyl group containing 6 to 24 carbon atoms. Suitable alkyl sulfates include, but are not limited to, sodium lauryl sulfate and sodium lauryl/myristyl sulfate.

Suitable alcohol sulfates that can be used in the cleaning composition include those having an alcohol group containing about 6 to about 24 carbon atoms.

The anionic surfactant can be neutralized with an alkaline metal salt, an amine, or a mixture thereof. Suitable alkaline metal salts include sodium, potassium, and magnesium. Suitable amines include monoethanolamine, triethanolamine, and monoisopropanolamine. If a mixture of salts is used, a suitable mixture of alkaline metal salt can be sodium and magnesium, and the molar ratio of sodium to magnesium can be between about 3:1 and about 1:1.

The cleaning composition, when provided as a concentrate, can include the additional anionic surfactant component in an amount sufficient to provide a use composition having desired wetting and detersive properties after dilution with water. The concentrate can contain about 0.1 wt. % to about 0.5 wt. %, about 0.1 wt. % to about 1.0 wt. %, about 1.0 wt. % to about 5 wt. %, about 5 wt. % to about 10 wt. %, about 10 wt. % to about 20 wt. %, 30 wt. %, about 0.5 wt. % to about 25 wt. %, and about 1 wt. % to about 15 wt. %, and similar intermediate concentrations of the anionic surfactant.

The cleaning composition can contain a nonionic surfactant component that includes a detersive amount of nonionic surfactant or a mixture of nonionic surfactants. Nonionic surfactants can be included in the cleaning composition to enhance grease removal properties. Although the surfactant component can include a nonionic surfactant component, it should be understood that the nonionic surfactant component can be excluded from the detergent composition.

Additional nonionic surfactants that can be used in the composition include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants include a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt %.

Other nonionic surfactants include alcohol alkoxylates. An suitable alcohol alkoxylate include linear alcohol ethoxylates such as Tomadol™ 1-5 which is a surfactant containing an alkyl group having 11 carbon atoms and 5 moles of ethylene oxide. Additional alcohol alkoxylates include alkylphenol ethoxylates, branched alcohol ethoxylates, secondary alcohol ethoxylates (e.g., Tergitol 15-S-7 from Dow Chemical), castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauric diethanolamide, polyethylene glycol cocoamide (e.g., PEG-6 cocoamide), oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglucosides, or mixtures thereof.

When nonionic surfactants are included in the detergent composition concentrate, they can be included in an amount of at least about 0.1 wt. % and can be included in an amount of up to about 15 wt. %. The concentrate can include about 0.1 to 1.0 wt. %, about 0.5 wt. % to about 12 wt. % or about 2 wt. % to about 10 wt. % of the nonionic surfactant.

Amphoteric surfactants can also be used to provide desired detersive properties. Suitable amphoteric surfactants that can be used include, but are not limited to: betaines, imidazolines, and propionates. Suitable amphoteric surfactants include, but are not limited to: sultaines, amphopropionates, amphodipropionates, aminopropionates, aminodipropionates, amphoacetates, amphodiacetates, and amphohydroxypropylsulfonates.

When the detergent composition includes an amphoteric surfactant, the amphoteric surfactant can be included in an amount of about 0.1 wt % to about 15 wt %. The concentrate can include about 0.1 wt % to about 1.0 wt %, 0.5 wt % to about 12 wt % or about 2 wt % to about 10 wt % of the amphoteric surfactant.

The cleaning composition can contain a cationic surfactant component that includes a detersive amount of cationic surfactant or a mixture of cationic surfactants. Cationic co-surfactants that can be used in the cleaning composition include, but are not limited to: amines such as primary, secondary and tertiary monoamines with $C_{18}$ alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and quaternary ammonium salts, as for example, alkylquaternary ammonium chloride surfactants such as n-alkyl($C_{12}$-$C_{18}$)dimethylbenzyl ammonium chloride, n-tetradecyldimethylbenzylammonium chloride monohydrate, and a naphthylene-substituted quaternary ammonium chloride such as dimethyl-1-naphthylmethylammonium chloride.

Builders—The cleaning compositions of the present invention may comprise one or more detergent builders or builder systems. When a builder is used, the subject composition will typically comprise at least about 1%, from about 5% to about 60% or even from about 10% to about 40% builder by weight of the subject composition. The detergent may contain an inorganic or organic detergent builder which counteracts the effects of calcium, or other ion, water hardness. Examples include the alkali metal citrates, succinates, malonates, carboxymethyl succinates, carboxylates, polycarboxylates and polyacetyl carboxylate; or sodium, potassium and lithium salts of oxydisuccinic acid, mellitic acid, benzene polycarboxylic acids, and citric acid; or citric acid and citrate salts. Organic phosphonate type sequestering agents such as DEQUEST® by Monsanto and alkanehydroxy phosphonates are useful. Other organic builders include higher molecular weight polymers and copolymers, e.g., polyacrylic acid, polymaleic acid, and polyacrylic/polymaleic acid copolymers and their salts, such as SOKALAN® by BASF. Generally, the builder may be up to 30%, or from about 1% to about 20%, or from about 3% to about 10%.

The compositions may also contain from about 0.01% to about 10%, or from about 2% to about 7%, or from about 3% to about 5% of a $C_{8-20}$ fatty acid as a builder. The fatty acid can also contain from about 1 to about 10 EO units. Suitable fatty acids are saturated and/or unsaturated and can be obtained from natural sources such a plant or animal esters (e.g., palm kernel oil, palm oil, coconut oil, babassu oil, safflower oil, tall oil, tallow and fish oils, grease, and mixtures thereof), or synthetically prepared (e.g., via the oxidation of petroleum or by hydrogenation of carbon monoxide via the Fisher Tropsch process). Useful fatty acids are saturated $C_{12}$ fatty acid, saturated $C_{12-14}$ fatty acids, saturated or unsaturated $C_{12-18}$ fatty acids, and a mixture thereof. Examples of suitable saturated fatty acids include capric, lauric, myristic, palmitic, stearic, arachidic and behenic acid. Suitable unsaturated fatty acids include: palmitoleic, oleic, linoleic, linolenic and ricinoleic acid.

Chelating Agents—The cleaning compositions herein may contain a chelating agent. Suitable chelating agents include copper, iron and/or manganese chelating agents and mixtures thereof. When a chelating agent is used, the subject composition may comprise from about 0.005% to about 15% or even from about 3.0% to about 10% chelating agent by weight of the subject composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Optical Brightener—In some embodiments, an optical brightener component, may be present in the compositions of the present invention. The optical brightener can include any brightener that is capable of eliminating graying and yellowing of fabrics. Typically, these substances attach to the fibers and bring about a brightening and simulated bleaching action by converting invisible ultraviolet radiation into visible longer-wave length light, the ultraviolet light absorbed from sunlight being irradiated as a pale bluish fluorescence and, together with the yellow shade of the grayed or yellowed laundry, producing pure white.

Fluorescent compounds belonging to the optical brightener family are typically aromatic or aromatic heterocyclic materials often containing condensed ring systems. An important feature of these compounds is the presence of an uninterrupted chain of conjugated double bonds associated with an aromatic ring. The number of such conjugated double bonds is dependent on substituents as well as the planarity of the fluorescent part of the molecule. Most brightener compounds are derivatives of stilbene or 4,4'-diamino stilbene, biphenyl, five membered heterocycles (triazoles, oxazoles, imidazoles, etc.) or six membered heterocycles (cumarins, naphthalamides, triazines, etc.).

Optical brighteners useful in the present invention are known and commercially available. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles and other miscellaneous agents. Examples of these types of brighteners are disclosed in "The Production and Application of Fluorescent Brightening Agents", M. Zahradnik, Published by John Wiley & Sons, New York (1982), the disclosure of which is incorporated herein by reference.

Stilbene derivatives which may be useful in the present invention include, but are not necessarily limited to, derivatives of bis(triazinyl)amino-stilbene; bisacylamino derivatives of stilbene; triazole derivatives of stilbene; oxadiazole derivatives of stilbene; oxazole derivatives of stilbene; and styryl derivatives of stilbene. In an embodiment, optical brighteners include stilbene derivatives.

In some embodiments, the optical brightener includes Tinopal UNPA, which is commercially available through the Ciba Geigy Corporation located in Switzerland.

Additional optical brighteners for use in the present invention include, but are not limited to, the classes of substance of 4,4'-diamino-2,2'-stilbenedisulfonic acids (flavonic acids), 4,4'-distyrylbiphenyls, methylumbelliferones, coumarins, dihydroquinolinones, 1,3-diarylpyrazolines, naphthalimides, benzoxazol, benzisoxazol and benzimidazol systems, and pyrene derivatives substituted by heterocycles, and the like. Suitable optical brightener levels include lower levels of from about 0.01, from about 0.05, from about 0.1 or even from about 0.2 wt % to upper levels of 0.5 or even 0.75 wt %.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Additional Enzymes—The cleaning compositions can comprise one or more enzymes which provide cleaning performance and/or fabric care benefits. Enzymes can be included herein for a wide variety of fabric laundering purposes, including removal of protein-based, carbohydrate-based, or triglyceride-based stains, for example, and/or for fabric restoration. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, amylases, or combinations thereof and may be of any suitable origin. The choice of enzyme(s) takes into account factors such as pH-activity, stability optima, thermostability, stability versus active detergents, chelants, builders, etc. A detersive enzyme mixture useful herein is a protease, lipase, cutinase and/or cellulase in conjunction with amylase. Sample detersive enzymes are described in U.S. Pat. No. 6,579,839.

Enzymes are normally present at up to about 5 mg, more typically from about 0.01 mg to about 3 mg by weight of active enzyme per gram of the detergent. Stated another way, the detergent herein will typically contain from about 0.001% to about 5%, or from about 0.01% to about 2%, or from about 0.05% to about 1% by weight of a commercial enzyme preparation. Protease enzymes are present at from about 0.005 to about 0.1 AU of activity per gram of detergent. Proteases useful herein include those like subtilisins from *Bacillus* [e.g. *subtilis, lentus, licheniformis, amyloliquefaciens* (BPN, BPN'), *alcalophilus,*] e.g. Esperase®, Alcalase®, Everlase® and Savinase® (Novozymes), BLAP and variants (Henkel). Further proteases are described in EP 130756, WO 91/06637, WO 95/10591 and WO 99/20726.

Amylases are described in GB Pat. #1 296 839, WO 94/02597 and WO 96/23873; and available as Purafect Ox Am® (Genencor), Termamyl®, Natalase®, Ban®, Fungamyl®, Duramyl® (all Novozymes), and RAPIDASE (International Bio-Synthetics, Inc).

The cellulase herein includes bacterial and/or fungal cellulases with a pH optimum between 5 and 9.5. Suitable cellulases are disclosed in U.S. Pat. No. 4,435,307 to Barbesgoard, et al., issued Mar. 6, 1984. Cellulases useful herein include bacterial or fungal cellulases, e.g. produced by *Humicola insolens*, particularly DSM 1800, e.g. 50 kD and ~43 kD (Carezyyme®). Additional suitable cellulases are the EGIII cellulases from *Trichoderma longibrachiatum*. WO 02/099091 by Novozymes describes an enzyme exhibiting endo-beta-glucanase activity (EC 3.2.1.4) endogenous to *Bacillus* sp., DSM 12648; for use in detergent and textile applications; and an anti-redeposition endoglucanase in WO 04/053039. Kao's EP 265 832 describes alkaline cellulase K, CMCase I and CMCase II isolated from a culture product of *Bacillus* sp KSM-635. Kao further describes in EP 1 350 843 (KSM 5237; 1139; KSM 64; KSM N131), EP 265 832A (KSM 635, FERM BP 1485) and EP 0 271 044 A (KSM 534, FERM BP 1508; KSM 539, FERM BP 1509; KSM 577, FERM BP 1510; KSM 521, FERM BP 1507; KSM 580, FERM BP 1511; KSM 588, FERM BP 1513; KSM 597, FERM BP 1514; KSM 522, FERM BP 1512; KSM 3445, FERM BP 1506; KSM 425. FERM BP 1505) readily-mass producible and high activity alkaline cellulases/endo-glucanases for an alkaline environment. Such endoglucanase may contain a polypeptide (or variant thereof) endogenous to one of the above *Bacillus* species. Other suitable cellulases are Family 44 Glycosyl Hydrolase enzymes exhibiting endo-beta-1,4-glucanase activity from Paenibacilus polyxyma (wild-type) such as XYG1006 described in WO 01/062903 or variants thereof. Carbohydrases useful herein include e.g. mannanase (see, e.g., U.S. Pat. No. 6,060,299), pectate lyase (see, e.g., WO99/27083), cyclomaltodextrin glucanotransferase (see, e.g., WO96/33267), and/or xyloglucanase (see, e.g., WO99/02663). Bleaching enzymes useful herein with enhancers include e.g. peroxidases, laccases, oxygenases, lipoxygenase (see, e.g., WO 95/26393), and/or (non-heme) haloperoxidases.

Suitable endoglucanases include: 1) An enzyme exhibiting endo-beta-1,4-glucanase activity (E.C. 3.2.1.4), with a sequence at least 90%, or at least 94%, or at least 97% or at least 99%, or 100% identity to the amino acid sequence of positions 1-773 of SEQ ID NO:2 in WO 02/099091; or a fragment thereof that has endo-beta-1,4-glucanase activity. GAP in the GCG program determines identity using a GAP creation penalty of 3.0 and GAP extension penalty of 0.1. See WO 02/099091 by Novozymes A/S on Dec. 12, 2002, e.g., Celluclean™ by Novozymes A/S. GCG refers to sequence analysis software package (Accelrys, San Diego, Calif., USA). GCG includes a program called GAP which uses the Needleman and Wunsch algorithm to find the alignment of two complete sequences that maximizes the number of matches and minimizes the number of gaps; and 2) Alkaline endoglucanase enzymes described in EP 1 350 843A published by Kao on Oct. 8, 2003 ([0011]-[0039] and examples 1-4).

Suitable lipases include those produced by *Pseudomonas* and *Chromobacter*, and LIPOLASE®, LIPOLASE ULTRA®, LIPOPRIME® and LIPEX® from Novozymes. See also Japanese Patent Application 53-20487, laid open on Feb. 24, 1978, available from Areario Pharmaceutical Co. Ltd., Nagoya, Japan, under the trade name Lipase P "Amano". Other commercial lipases include Amano-CES, lipases ex *Chromobacter viscosum*, available from Toyo Jozo Co., Tagata, Japan; and *Chromobacter viscosum* lipases from U.S. Biochemical Corp., U.S.A. and Diosynth Co., The Netherlands, and lipases ex *Pseudomonas gladioli*. Also suitable are cutinases [EC 3.1.1.50] and esterases.

Enzymes useful for liquid detergent formulations, and their incorporation into such formulations, are disclosed in U.S. Pat. No. 4,261,868 to Hora, et al., issued Apr. 14, 1981. In an embodiment, the liquid composition herein is substantially free of (i.e. contains no measurable amount of) wild-type protease enzymes. A typical combination is an enzyme cocktail that may comprise, for example, a protease and lipase in conjunction with amylase. When present in a cleaning composition, the aforementioned additional enzymes may be present at levels from about 0.00001% to about 2%, from about 0.0001% to about 1% or even from about 0.001% to about 0.5% enzyme protein by weight of the composition.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

A useful enzyme stabilizer system is a calcium and/or magnesium compound, boron compounds and substituted boric acids, aromatic borate esters, peptides and peptide derivatives, polyols, low molecular weight carboxylates, relatively hydrophobic organic compounds [e.g. certain esters, diakyl glycol ethers, alcohols or alcohol alkoxylates], alkyl ether carboxylate in addition to a calcium ion source, benzamidine hypochlorite, lower aliphatic alcohols and carboxylic acids, N,N-bis(carboxymethyl) serine salts; (meth) acrylic acid-(meth)acrylic acid ester copolymer and PEG; lignin compound, polyamide oligomer, glycolic acid or its salts; poly hexa methylene bi guanide or N,N-bis-3-amino-propyl-dodecyl amine or salt; and mixtures thereof. The detergent may contain a reversible protease inhibitor e.g., peptide or protein type, or a modified subtilisin inhibitor of family VI and the plasminostrepin; leupeptin, peptide trifluoromethyl ketone, or a peptide aldehyde. Enzyme stabilizers are present from about 1 to about 30, or from about 2 to about 20, or from about 5 to about 15, or from about 8 to about 12, millimoles of stabilizer ions per liter.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936; 5,595, 967. Such cobalt catalysts are readily prepared by known procedures, such as taught for example in U.S. Pat. Nos. 5,597,936, and 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof. In some embodiments, the solvent includes water. The water can include water from any source including deionized water, tap water, softened water, and combinations thereof. Solvents are typically present at from about 0.1% to about 50%, or from about 0.5% to about 35%, or from about 1% to about 15% by weight.

Form of the Compositions

The detergent compositions of the present invention may be of any suitable form, including paste, liquid, solid (such as tablets, powder/granules), foam or gel, with powders and tablets being preferred. The composition may be in the form of a unit dose product, i.e. a form which is designed to be used as a single portion of detergent composition in a washing operation. Of course, one or more of such single portions may be used in a cleaning operation.

Solid forms include, for example, in the form of a tablet, rod, ball or lozenge. The composition may be a particulate form, loose or pressed to shape or may be formed by injection molding or by casting or by extrusion. The composition may be encased in a water soluble wrapping, for, example of PVOH or a cellulosic material. The solid product may be provided as a portioned product as desired.

The composition may also be in paste, gel or liquid form, including unit dose (portioned products) products. Examples include a paste, gel or liquid product at least partially surrounded by, and preferably substantially enclosed in a water-soluble coating, such as a polyvinyl alcohol package. This package may for instance take the form of a capsule, a pouch or a moulded casing (such as an injection moulded casing) etc. Preferably the composition is substantially surrounded by such a package, most preferably totally surrounded by such a package. Any such package may contain one or more product formats as referred to herein and the package may contain one or more compartments as desired, for example two, three or four compartments.

If the composition is a foam, a liquid or a gel it is preferably an aqueous composition although any suitable solvent may be used. According to an especially preferred embodiment of the present invention the composition is in the form of a tablet, most especially a tablet made from compressed particulate material.

If the compositions are in the form of a viscous liquid or gel they preferably have a viscosity of at least 50 mPas when measured with a Brookfield RV Viscometer at 25° C. with Spindle 1 at 30 rpm.

The compositions of the invention will typically be used by placing them in a detergent dispenser e.g. in a dishwasher machine draw or free standing dispensing device in an automatic dishwashing machine. However, if the composition is in the form of a foam, liquid or gel then it may be applied to by any additional suitable means into the dishwashing machine, for example by a trigger spray, squeeze bottle or an aerosol.

Processes of Making Cleaning Compositions

The compositions of the invention may be made by any suitable method depending upon their format. Suitable manufacturing methods for detergent compositions are well known in the art, non-limiting examples of which are described in U.S. Pat. Nos. 5,879,584; 5,691,297; 5,574,005; 5,569,645; 5,565,422; 5,516,448; 5,489,392; and 5,486,303. Various techniques for forming detergent compositions in solid forms are also well known in the art, for example, detergent tablets may be made by compacting granular/particular material and may be used herein.

In one aspect, the liquid detergent compositions disclosed herein may be prepared by combining the components thereof in any convenient order and by mixing, e.g., agitating, the resulting component combination to form a phase stable liquid detergent composition. In one aspect, a liquid matrix is formed containing at least a major proportion, or even substantially all, of the liquid components, with the liquid components being thoroughly admixed by imparting shear agitation to this liquid combination. For example, rapid stirring with a mechanical stirrer may usefully be employed. While shear agitation is maintained, substantially all of any anionic surfactant and the solid ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills are incorporated. As a variation of the composition preparation procedure described above, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

Reduction of Smoking in Laundry Fabrics

There have been reports of undesirable smoking issues for laundry particularly when a washed fabric comes in contact with a hot iron. This is due to a switch from nonyl phenol ethoxylate (NPE) based detergents to alcohol phenol ethoxylate (APE) based detergents. The problem is due to the residual unreacted long chain alcohols which are highly soluble in APE based detergents. It is well known in the surfactant industry that APEs are more monodisperse and have less unreacted alcohol than the AEs, because the starting alkyl phenols are more reactive than the starting linear alcohols. The use solution cannot suspend all the highly insoluble unreacted alcohol, which deposits onto a washed fabric and can cause smoking when the fabric comes in contact with a hot iron.

The extended surfactants and microemulsions of the present invention undergo two steps of alkoxylation (first propoxylation or butoxylation, then followed with ethoxylation) and therefore have reduced levels of residual (unreacted) alcohol, specifically below 0.1%. Thus after the laundry process, the extended surfactants and microemulsions of the present invention leave less residue from the highly insoluble long chain alcohols onto the washed fabric, which in turn greatly reduces the smoking when these washed fabrics come in contact with hot irons.

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques. All references cited herein are hereby incorporated in their entirety by reference.

EXAMPLES

In an effort to reduce energy consumption and total water use, laundry systems in health and home care and textile care need water reclaim systems. Previous foam fractionation work obtained very good results with Vehicle Care produced water. Textile care produced water, however contains high levels of strongly emulsified oil. High levels of soil and detergent lead to a more challenging application. See FIG. 1. Applicants herein provide a faster demulsification trigger, without sacrificing cleaning performance for textile cleaning and water reclamation.

Tomamine DA14 (Isodecycloxypropyl-1,3-diaminopropane), and DA17 (Isotridecyloxypropyl-1,3-diaminopropane) and E-14-2 (bis-(2-hydroxyethyl) isodecyloxypropylamine) are ether diamines or triamines designed for the selective removal of silica during ore flotation, commercially available from Air Products and Chemicals, Inc. Allentown, Pennsylvania.

Tomadol 91-2.5 is a nonionic ethoxylated alcohol surfactant with carbon chain length of C9, C10, and/or C11 with 2.5 average moles of ethylene oxide per mole of alcohol commercially available from Air Products and Chemicals, Inc. Allentown, Pennsylvania.

Lonzabac 12.100 (N-(3-aminopropyl)-N-dodecylpropane-1,3-diamine) is a disinfectant for food processing industry, institutions, hospitals (commercially available from Lonza, Inc. Allendale, New Jersey.

Ecosurf EH-3 is ECOSURF™ EH-3 is an alcohol ethoxylate nonionic surfactant commercially available from Dow chemical, Inc. Midland, Michigan.

Surfonic PEA 25 is a SURFONIC® PEA 25 tertiary amine alkoxylate-oil soluble lubricant commercially available from Huntsmen International LLC, the Woodlands, Texas.

Turboflex D and TurboFlex D-AE, are commercially available detergent compositions that are NPE free commercially available from Ecolab, Inc. St. Paul Minnesota.

Example 1

Amine Surfactants as "Universal" Co-Surfactant for Anionic Extended Surfactants for Multiple Oil Phases:

Table 2 summarizes microemulsion data obtained for a surfactant package based on 1.6667 parts X-AES extended anionic surfactant $C_{12-14}$—$(PO)_{16}$-$(EO)_2$-sulfate to/1 part Tomamine DA-14, and 0.75 part Tomadol 91-2.5 (all actives). This composition forms clear, flow able microemulsions with 3 entire different oil phases—soybean oil, mineral oil, and motor oil, and also mixture of soybean oil and mineral oil, from room temperature to 120° F.

TABLE 2

Microemulsion—Extended anionic surfactant + amine based co-surfactant

| | EXP 1 | EXP 2 | EXP 3 | EXP 4 |
|---|---|---|---|---|
| Soybean Oil | 5 | | 2.5 | |
| Mineral Oil | | 5 | 2.5 | |
| Motor Oil | | | | 5 |
| DI Water | 5 | 5 | 5 | 5 |
| X-AES $C_{12-14}$-$(PO)_{16}$-$(EO)_2$-sulfate | 1.6667 | 1.6667 | 1.6667 | 1.6667 |
| Tomamine DA-14 | 1 | 1 | 1 | 1 |
| Tomadol 91-2.5 | 0.75 | 0.75 | 0.75 | 0.75 |
| Microemulsion Temp | 120-RT | 120-RT | 120-RT | NEAR |

Figure 2:
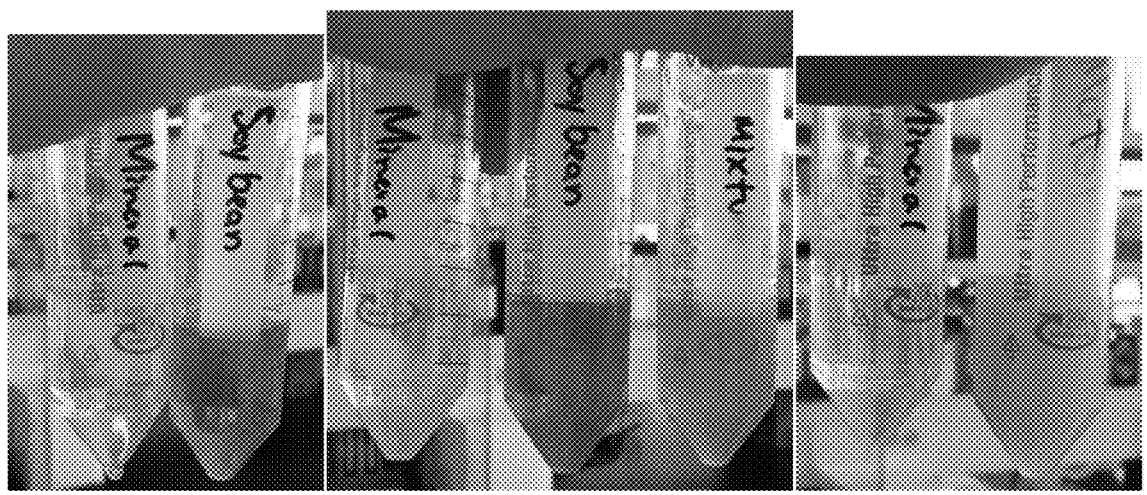
FIG. 2 is a photograph of the microemulsions formed from 1.6667 parts X-AES (extended anionic surfactant $C_{12-14}$—$(PO)_{16}$-$(EO)_2$-sulfate) to/1 part Tomamine DA-14 (Isodecycloxypropyl-1,3-diaminopropane), and 0.75 part Tomadol 91-2.5 (ethoxylated alcohol surfactant with carbon chain length of C9, C10, and/or C11 with 2.5 average moles of ethylene oxide per mole of alcohol)(all actives). This composition forms clear, flow able microemulsions with 3 entire different oil phases—soybean oil, mineral oil, and motor oil, and also mixture of soybean oil and mineral oil, from room temperature to 120°.

FIG. 2 is a photograph of the microemulsions formed. One can see that the solutions are stable with no precipitation. For mineral oil, soybean oil, a mixture of the two and even motor oil. One can see that synergistic combinations of an extended anionic sulfate surfactant (X-AES) with amine surfactants form versatile microemulsification platform.

Figure 3:
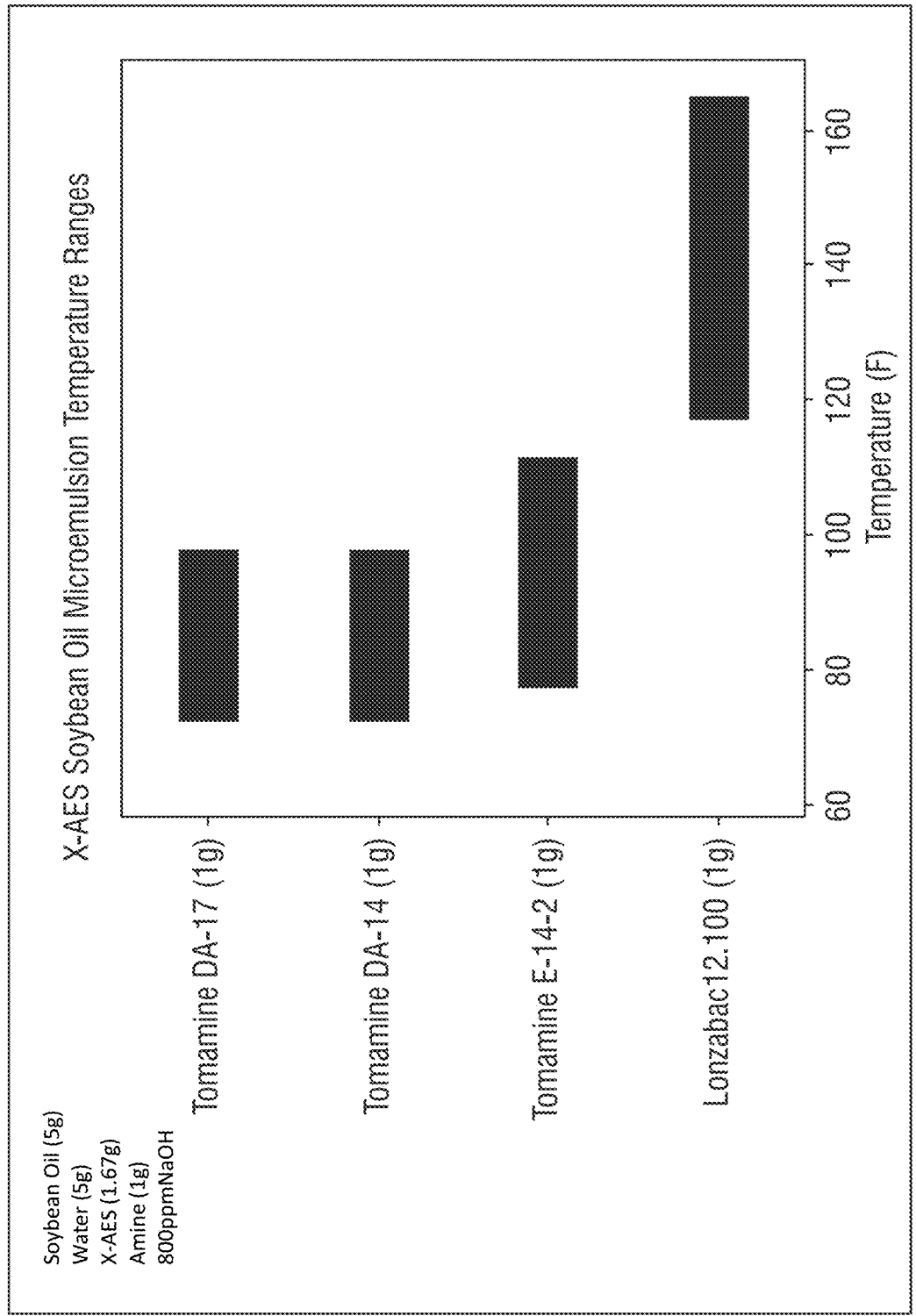
FIG. 3 is a graph summarizing soybean oil microemulsion data for surfactant packages of X-AES with a series of amine co-surfactants. These data show that the temperature range of microemulsion formation can be controlled by using different amine co-surfactants.

FIG. 3 is a graph summarizing soybean oil microemulsion data for surfactant packages of X-AES with a series of amine co-surfactants. These data show that the temperature range of microemulsion formation can be controlled by using different amine co-surfactants. For example, N-(3-aminopropyl)-N-dodecylpropane-1,3-diamine as a cosurfactant allows for stable microemulsions at temperatures from 120 degrees F. to 165 degrees F. Isodecycloxypropyl-1,3-diaminopropane), and DA17 (Isotridecyloxypropyl-1,3-diaminopropane as co surfactants have lower temperature ranges of about 70-115 degree F., while bis-(2-hydroxyethyl) isodecyloxypropylamine has a microemulsion temperature range of 75 to 120 degree F. From this we can ascertain that straight chain higher amounts of branching lead to higher temperature stability of the emulsions. It is also important to note that Lonzabac 12.100 is an effective antimicrobial. Therefore, the package of X-AES and Lonzabac 12.100 is an excellent cleaner/antimicrobial combination.

Example 2

Figure 4:
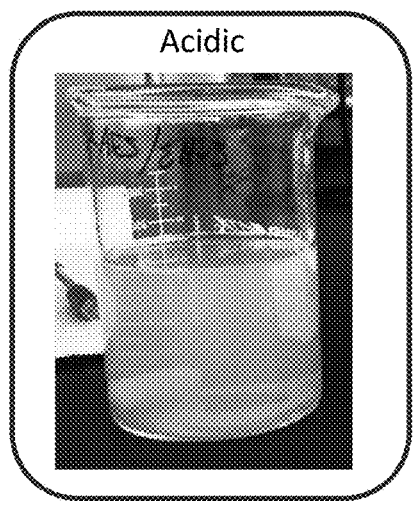
FIG. 4 is a photograph of a solution of 500 ppm Active Soybean oil microemulsion with X-AES as main surfactant and Ecosurf EH-3 as (non-ionic) co-surfactant. 5 gpg water was used at a temperature of 120 F for test. The microemulsion remains stable even when adjusted from alkaline to acidic conditions.

Strategic Emulsion Breaking with pH Effect on the Amine Co-Surfactants 1500 ppm Active Soybean oil microemulsion with X-AES as main surfactant and Ecosurf EH-3 as (non-ionic) co-surfactant was created according to the invention. 5 gpg Water at 120 F was used for testing. The results are shown in FIG. 4. One can see that the microemulsion remains stable even when adjusted from alkaline to acidic conditions.

Figure 5:
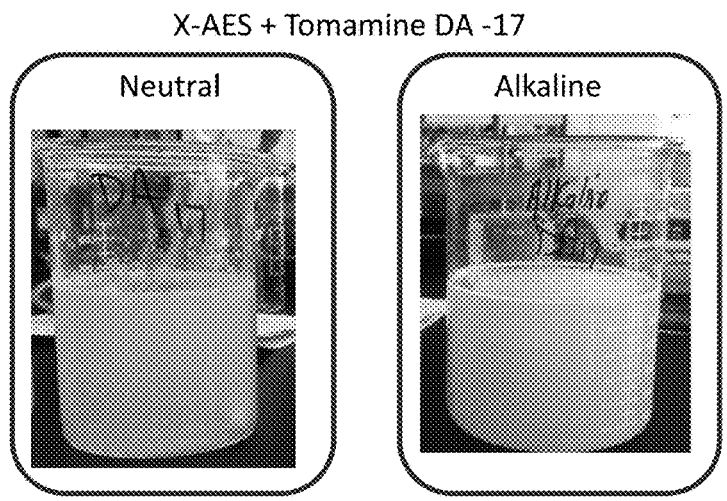
FIG. 5 is a photograph of microemulsions formed with of X-AES+Tomamine DA-17 (Isotridecyloxypropyl-1,3-diaminopropane) one can see that the use of this cosurfactant results in emulsions that are more stable under alkaline conditions.

Next 1500 ppm Active Soybean bean oil was used with 5 gpg Water at 120° F. The results are shown in photographs as FIGS. 5 and 6 at time zero. In contrast to use of the nonionic cosurfactant, when amine co-surfactants are used in the microemulsions with X-AES, the emulsions were stable at alkaline conditions but instantly separated under acidic or neutral pH.

Figure 6:
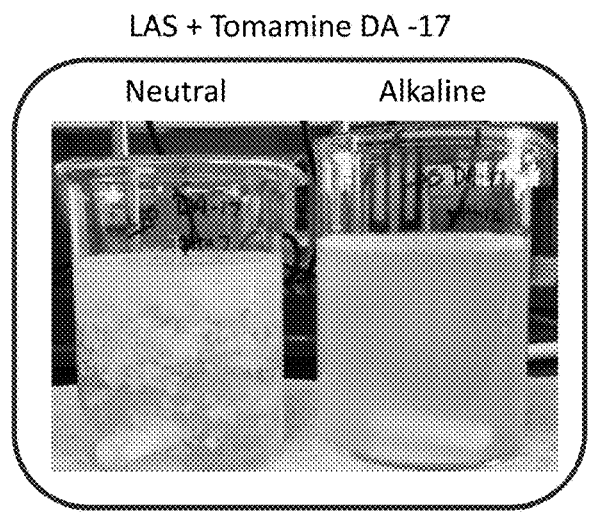
FIG. 6 is a photograph of LAS linear alkylbenzene sulfonaies+Tomamine DA-17. At alkaline conditions, the surfactants form a stable emulsion with soybean oil. The emulsion formed is nearly completely precipitated at neutral pH. Under alkaline conditions a stable emulsion is formed. A pH shift to neutral conditions causes immediate precipitation formation and emulsion destabilization.

There exists an antagonist interaction between long chain sulfates and the protonated amine-co-surfactants. Further, LAS linear alkylbenzene sulfonates+Tomamine DA-17 cannot form microemulsion with soybean oil. The emulsion formed is nearly completely precipitated at neutral pH (FIG. 6). The microemulsion formed with of X-AES+Tomamine DA-17 is more stable under alkaline conditions.

However, a pH shift to neutral conditions causes immediate precipitation formation and emulsion destabilization (FIG. 6).

Figure 7:
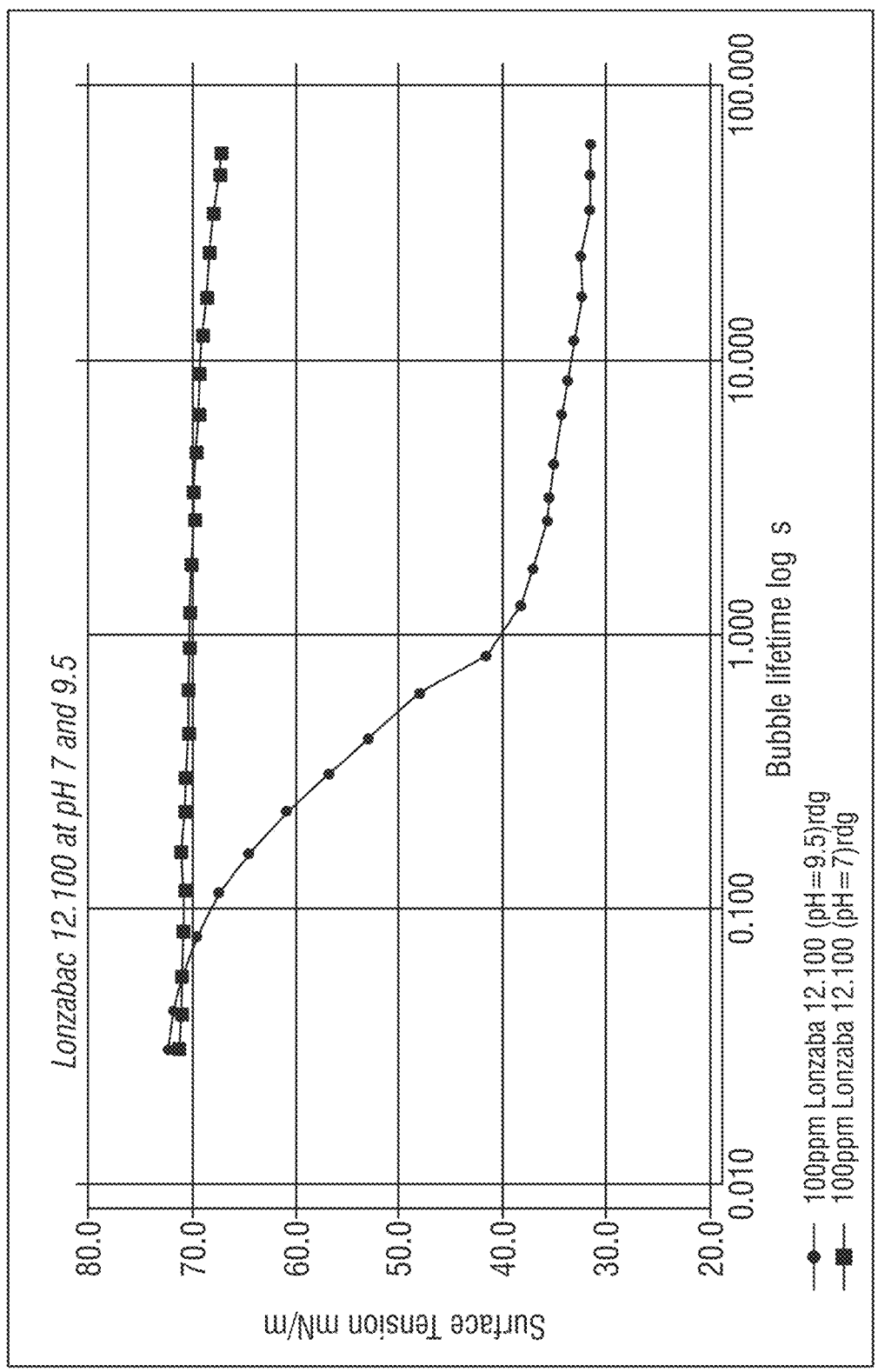
FIG. 7 is a graph of the dynamic surface tension vs. bubble lifetime for Lonzabac 12.100 (N-(3-aminopropyl)-N-dodecylpropane-1,3-diamine) at 100 ppm at pH 7 and pH 9.5. At alkaline pH, this triamine surfactant is very dynamically surface active and the surface tension is decreased. At neutral pH (partially protonated form) the triamine surfactant is significantly less dynamically surface active.

Microemulsions formed with nonionic co-surfactants, were extremely stable both to dilution and pH changes. The nature of amine surfactants allows for selective synergy—emulsification and pH sensitivity, especially in the presence of an anionic surfactants. FIG. 7 shows the effects of a simple pH shift on the solution phase behavior. The effects are drastic. Amine based surfactants are sensitive to pH because they are susceptible to protonation, pKb. The dynamic surface tension graph in FIG. 7 illustrates this phenomenon. At alkaline pH (neutral form), the amine surfactant is dynamically active. At neutral pH (protonated form), the amine surfactant is no longer dynamically active.

RESULTS AND CONCLUSIONS

The results illustrate that excellent cleaning compositions can be strategically formulated based on an anionic extended surfactant with an amine co-surfactants. These can be anti-microbial compositions with certain amine co-surfactants such as Lonzabac 12.100. These compositions have a built-in pH trigger for ultra-fast demulsification, because the protonated amine surfactant causes quat-anionic in-activation. These compositions represent both detergent and post detergent water treatment formulations as they provide excellent cleaning as well as ease of water treatment.

The results show that an extended surfactant is critical for microemulsion formation with triglyceride oil. A certain length of extension (moles of PO in the middle) is necessary. The required extension length is somewhere between 5 and 8 moles PO, however, the extended surfactant alone is not enough. An appropriate co-surfactant is critical.

Applicant's invention relates to new novel amine co-surfactants including:
- alkyl amines, alkyl diamines, and alkyl triamines; especially when the alkyl is branched such as isodecyl, isotridecyl to increase the effective cross-sectional area of the hydrophobe; alkyl amines, alkyl diamines, and alkyl triamines; including linear alkyl chains, such as dodecyl; and Medium chain amine with low moles of ethoxylation.

Because of the strong hydrogen bonding of the anionic charge group (worst for more water loving groups such as sulfate). It is very difficult, if not impossible, to form a liquid emulsion of equal portion active water/anionic surfactant/triglyceride. Applicants have overcome this obstacle with the use of long enough PO extension on the anionic surfactant, greatly minimizing the formation of paste. The PO extension increases fluidity and greatly reduces interfacial viscoelasticity. The viscoelasticity reducing effect is enhanced with the further combination with novel co-surfactants.

The combined use of an anionic surfactant with enough PO extension as the main surfactant, and novel co-surfactants with the right structures as the minor component, can form liquid single phase microemulsions. The novel co-surfactants include alkyl oxypropyl amines, diamines, and triamine, alkyl amines, diamines, and triamines, either may have low moles ethoxylation (extended nonionic amine surfactants such as Surfonic PEA-25) and a mixture there of. These compositions are effective in forming microemulsions with oily soils, even the tough to 'microemulsify" non-transfats such as fresh and used soybean oils, facilitating their eventual removal from a substrate.

These compositions are also expected to provide ultra-low interfacial tensions with oils and be useful in the Energy applications such as Enhanced Oil Recovery.

The amine co-surfactants act as "universal" co-surfactants since each extended anionic and amine surfactant combination form microemulsions with a variety of oil phases at similar temperature ranges. Without being bound by theory, we speculate that some of the amine molecules are protonated (even at higher pH), thus aiding the interfacial packing through quat-anionic synergy.

Because of the nature of amine co-surfactants and their relatively high Kb, they can be strategically protonated at neutral conditions. The combined use of an extended anionic surfactant and amine co-surfactant offer micro-emulsification in alkaline conditions, followed by rapid emulsion breaking at neutral conditions.

As shown in FIG. 7, pH drastically affects the dynamic surface activity of Lonzabac 12.100. At pH 7.5, the amine(s) in the partial protonated form cause a drastic reduction in dynamic surface activity. The antagonist relationship between long chain sulfates and medium to long chain protonated amines facilitates quick emulsion breaking (FIG. 8). The combined use of both extended anionic and extended non-ionic surfactants, preferably with a co-surfactant, is the most efficient in forming microemulsions with non-transfat oils.

What is claimed is:

1. A laundry detergent composition comprising:
   a builder;
   an enzyme; and
   a surfactant system comprising an extended chain $C_{12}$-$C_{14}$ alkyl anionic sulfate surfactant having 5 or more moles of propoxylation; one or more amine co-surfactants comprising: an alkyl oxypropyl diamine, wherein the amine co-surfactant has a branched isodecyl or isotridecyl group; and
   an extended nonionic ethoxylated or ethoxylated and propoxylated $C_8$-$C_{11}$ alcohol surfactant having from 1 to 10 moles of ethoxylation,
   wherein the extended chain $C_{12}$-$C_{14}$ alkyl anionic sulfate surfactant and the amine co-surfactant and the extended nonionic ethoxylated or ethoxylated and propoxylated $C_8$-$C_{11}$ alcohol surfactant have a weight ratio of 1.67: 1:0.75,
   wherein said surfactant system forms an emulsion or microemulsion with an oily soil when the amine co-surfactant is neutral and precipitates with oily soil when the amine co-surfactant is protonated.

2. The laundry detergent composition of claim 1, wherein said soil is a non-transfat oil or soybean oil.

3. The laundry detergent composition of claim 1, wherein said laundry detergent composition is employed under alkaline or acidic conditions.

4. The laundry detergent composition of claim 1, wherein said diamine has from about 1 to about 3 moles of ethoxylation.

5. The laundry detergent composition of claim 1, wherein said microemulsion is stable at a temperature of from about 120° F. to about 140° F.

6. The laundry detergent composition of claim 1, wherein said co-surfactant is isodecyloxypropyl-1,3-diaminopropane, or isotridecyloxypropyl-1,3-diaminopropane, and wherein said microemulsion is stable from about 75° F. to about 105° F.

7. The laundry detergent composition of claim 1, wherein said microemulsion is stable from 80 to 115° F. and said cosurfactant is bis-(2-hydroxyethyl) isodecyloxypropylamine.

8. The laundry detergent composition of claim 1, wherein said extended anionic surfactant comprises a compound of formula:

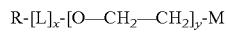

where R is a linear or branched, saturated or unsaturated, substituted or unsubstituted, aliphatic or aromatic hydrocarbon radical having from about 6 to 20 carbon atoms, L is a linking group, M is a carboxylate, a sulfonate, a sulfate, a phosphate, or a phosphonate, x is the chain length of the linking group ranging from 2-16, and y is the average degree of ethoxylation ranging from 1 to 5.

9. The laundry detergent composition of claim 1, wherein the co-surfactants comprise 5 or more moles of propoxylation.

10. The laundry detergent composition of claim 1, wherein said extended surfactant is $C_{12}$—$(PO)_{16}$-$(EO)_2$ sulfate.

* * * * *